US011484583B2

(12) United States Patent
Feng et al.

(10) Patent No.: US 11,484,583 B2
(45) Date of Patent: Nov. 1, 2022

(54) **INTESTINAL BACTERIA *BUTYRIBACTER INTESTINI* AND APPLICATION THEREOF**

(71) Applicant: BGI Shenzhen, Shenzhen (CN)

(72) Inventors: Qiang Feng, Shenzhen (CN); Wenbin Xue, Shenzhen (CN); Yuanqiang Zou, Shenzhen (CN); Xiaoping Li, Shenzhen (CN); Chuan Liu, Shenzhen (CN); Xin Li, Shenzhen (CN)

(73) Assignee: BGI SHENZHEN, Shenzhen (CN)

( * ) Notice: Subject to any disclaimer, the term of this patent is extended or adjusted under 35 U.S.C. 154(b) by 0 days.

(21) Appl. No.: 17/174,053

(22) Filed: Feb. 11, 2021

(65) Prior Publication Data

US 2021/0170009 A1 Jun. 10, 2021

Related U.S. Application Data

(63) Continuation of application No. 15/755,926, filed as application No. PCT/CN2016/076878 on Mar. 21, 2016, now Pat. No. 11,033,614.

(30) Foreign Application Priority Data

Aug. 27, 2015 (CN) .......................... 201510536315.2

(51) Int. Cl.
  *A61K 39/08* (2006.01)
  *C12N 1/20* (2006.01)
  *A61K 35/741* (2015.01)
  *A61K 9/00* (2006.01)

(52) U.S. Cl.
  CPC ................ *A61K 39/08* (2013.01); *A61K 9/00* (2013.01); *A61K 35/741* (2013.01); *C12N 1/20* (2013.01)

(58) Field of Classification Search
  None
  See application file for complete search history.

(56) References Cited

FOREIGN PATENT DOCUMENTS

| CN | 102234664 A | 11/2011 |
|---|---|---|
| CN | 101624611 B | 8/2012 |
| CN | 103815408 A | 5/2014 |
| CN | 104415061 A | 3/2015 |
| WO | 2010/093262 A1 | 8/2010 |

OTHER PUBLICATIONS

Office Action issued for EP patent application 16838248.9, dated Mar. 14, 2019.
Kabuki, T., et al. "Characterization of a bacteriocin,Thermophilin 1277,produced by *Streptococcus thermophilus* SBT1277" (2006) Journal of Applied Microbiology 102 (2007) 971-980.
Office Action issued for JP patent application 2018-510948, dated May 2, 2019 with English Translation.
Liu, L., et al. "Experimental Study On Combination of Lactobacilli Strain and Clostridium butyricum Strain in Treatment of Acute Ulcerative Colitis in Mice" Practical Preventive Medicine, Aug. 2009, vol. 16, No. 4, 1255-1258, with English Abstract.
Sang, Y., et al. "The effect of Clostridium butyricum on expression of chemokines RANTES and MCP-1 in murine intestinal mucosa with ulcerative colitis" Shanxi Med J. Dec. 2009, vol. 38, No. 12, 1075-1078, with English Abstract.
Kuroiwa, Toyoaki et al. "Inhibition of Enteropathogens by Clostridium butyricum MIYAIRI 588" Journal of Infectious Diseases (1990), vol. 64 No. 3, pp. 257-263.
Science of lactic acid bacteria (Feb. 7, 2002) MIYARISAN Pharmaceutical Co., Ltd, retrieved on Jan. 23, 2019, retrieved from the Internet, URL: http://www.miyarisan.com/probiotics.htm.
The Science of Obesity; The Japanese Association of Medical Sciences symposium recording; Scientific, 2003, one hundred twenty fourth The Japanese Association of Medical Sciences symposium recording [Jan. 1, 2006], p. 37.
Budak et al. "Effects of Apple Cider Vinegars Produced with Different Techniques on Blood Lipids in High-Cholesterol-Fed-Rats" (2011) J Agric Food Chem, 59:6638-6644.
Yang, "Metabolism of single carbon substances by Butyribacterium methylotrophicum," Journal of Microbiology 18(1), four pages, Mar. 31, 1998.
Yan et al. "Expression of Solvent-Forming Enzynes and Onset of Solvent Production in Batch Cultures of Clostridium beijerinckii ("*Clostridium butylicum*")" (1988) Appl. Environ. Microbiol. 54:642-648.
Written Opinion of the International Searching Authority dated Jun. 28, 2016, corresponding to PCT/CN2016/076878, with English Translation.
International Search Report dated Jun. 28, 2016, corresponding to PCT/CN2016/076878, with English Translation.

*Primary Examiner* — Brian Gangle
(74) *Attorney, Agent, or Firm* — Westman, Champlin & Koehler, P.A.; Z. Peter Sawicki; Amanda M. Prose

(57) ABSTRACT

Provided is an application of *Butyribacter intestini* in the treatment and prevention of obesity-related diseases. Also provided is a composition for the treatment and prevention of obesity and obesity-related diseases.

17 Claims, 3 Drawing Sheets

Specification includes a Sequence Listing.

US 11,484,583 B2

INTESTINAL BACTERIA *BUTYRIBACTER INTESTINI* AND APPLICATION THEREOF

TECHNICAL FIELD

The present invention relates to the field of microbiology. In particular, the present invention relates to a use of *Butyribacter* (*Butyribacter intestini*) in the treatment and prevention of obesity as well as the associated diseases thereof, and also relates to a composition comprising *Butyribacter* and the use thereof.

BACKGROUND

There are a large number of micro-organisms in a human body living in symbiosis, and most of them live in the human intestinal tract, with a quantity of more than 1000 trillion ($10^{14}$ orders of magnitude), which is more than 10 times the total number of human cells. During the long evolution process, intestinal microbes have achieved a good cooperation with human beings and played a crucial role in the nutrition, metabolism and immunity of the body. Many researchers regard human intestinal microflora more as an organ of the human body or the second genome of the human body, and in which the massive genetic information contained is closely related to human health. Research on nearly ten thousand samples from hundreds of diseases such as diabetes, coronary heart disease, obesity, colon cancer and so on has shown that some specific species have exhibited a significant correlation with those diseases. These results provide a brand new direction for the clinical evaluation and the diagnosis, as well as the post-intervention treatment of the diseases.

Obesity, a chronic disease, is a result of many factors. The origin of the disease is unknown so far. Obesity is also an inducing factor for a series of diseases, such as hypertension, diabetes, coronary heart disease, cholecystopathy, osteoarthritis, sleep apnea, respiratory disorders, hysteroma, prostate cancer, breast cancer and colon cancer etc. According to a report by the NIH, currently, there are about 97 million Americans either overweight and/or suffering from obesity, wherein the number of obesity-associated type II diabetes patients goes up to about 150 million, and about 200,000 people die from obesity-associated diseases each year.

Generally, obesity is a result of excessive body fat due to physical or biochemical functional changes. The fat accumulates when the energy intake is greater than the energy consumption. Pathogenically, there are two types of obesity: (a) simple obesity and (b) second obesity. Simple obesity can be divided into idiopathic obesity and acquired obesity. The number of simple obesity patients accounts for more than 95% of the total number of obesity patients. idiopathic obesity is caused by the massive number of adipocyte and is commonly seen in childhood obesity. Acquired obesity is caused by the larger size of adipocyte and commonly occurs in adulthood obesity. Secondary obesity, also known as symptomatic obesity, is usually caused by endocrinic or metabolic diseases.

There are currently five strategies for treating obesity: dieting, exercise, behavioral therapy, medication and therapeutic operation. Depending on the patient's risk factors for health and the rate and effectiveness of weight loss, these strategies can be selected or combined to treat obese patients. The rate and effectiveness of weight loss are influenced by many factors such as age, height, family history, risk factors and so on. Dieting-Exercise therapy, that is, low-calorie and low-fat food intake and aerobic exercises, however, this method is generally considered unsuccessful to the general public and requires long-term and regular persistence; the surgery for removal of body fat can achieve immediate effects, but there are many limitations, such as surgical risk, unsustainable fat removal effect and costly expense, etc.

Medication is currently the main therapy for clinical treatment of obesity and the obesity-associated diseases (such as diabetes). Mechanisms of medication include suppressing appetite, increasing energy consumption, stimulating adipokinesis, reducing triglyceride synthesis and inhibiting fat absorption. At present, the main drugs are: phenylpropanolamine (PPA), orlistat (Xenical III) and sibutramine (Reductil™). Hyperglycemia in some diabetics may still not be adequately controlled through dieting and/or exercise therapy or using the above therapeutic compounds. For these patients, exogenous insulin should be used. For patients, the use of exogenous insulin is very expensive and painful, and can cause complications for the patient. For example, miscalculation of an insulin dose leads to insulin response (hypoglycemia) due to an empty stomach or irregular exercises. In addition, local or systemic allergy or immunological resistance to the drug may also be induced by the drug application.

So far, no method or medication in the art can be used with little side effect for effectively treating or preventing obesity and the associated diseases thereof.

Therefore, there is an urgent need in the art to develop a new medication that is non-toxic and without side effects for the treatment and prevention of obesity and the associated diseases.

SUMMARY OF INVENTION

Another object of the present invention is to provide a use of *Butyribacter* in the treatment and prevention of obesity and obesity-associated diseases.

Another object of the present invention is to provide an effective pharmaceutical, beverage, food composition, or animal feed composition without toxic or side-effect for treating and preventing obesity and obesity-associated diseases.

Another object of the present invention is to provide a method for reducing body weight and/or blood glucose and the use thereof.

The first aspect of the present invention is to provide a *Butyribacter*, which is *Butyribacter intestini*.

In another preferred embodiment, the sequence of 16srDNA of *Butyribacter* is as set forth by SEQ ID NO.: 1.

In another preferred embodiment, the *Butyribacter* is *Butyribacter intestini* TF01-11 with a deposit number of CGMCC 10984.

The second aspect of the present invention is to provide a composition comprising: (a) a safe and effective amount of *Butyribacter* and/or metabolites thereof according to the first aspect of the present invention; and (b) a food acceptable carrier or a pharmaceutically acceptable carrier.

In another preferred embodiment, the composition is selected from the group consisting of: a food composition, a health care composition, a pharmaceutical composition, a beverage composition, a feed composition, and a combination thereof.

In another preferred embodiment, the composition is an oral preparation.

In another preferred embodiment, the composition is a liquid preparation, a solid preparation, or a semi-solid preparation.

In another preferred embodiment, the dosage form of the composition is selected from the group consisting of a powder, pulvis, tablet, sugar coating agent, capsule, granule, suspension, solution, syrup, drop, and sublingual tablet.

In another preferred embodiment, the food composition comprises an emulsion product, a solution product, a powder product, or a suspension product.

In another preferred embodiment, the food composition comprises a dairy product, milk powder, or lotion.

In another preferred embodiment, the liquid preparation is selected from the group consisting of a solution product or a suspension product.

In another preferred embodiment, the composition comprises $1\times10$-$1\times10^{20}$ cfu/mL or cfu/g of *Butyribacter intestini* TF01-11, preferably $1\times10^{4}$-$1\times10^{15}$ cfu/mL or cfu/g of *Butyribacter intestini* TF01-11, based on the total volume or total weight of the composition.

In another preferred embodiment, the composition comprises from 0.0001 to 99 wt %, preferably from 0.1 to 90 wt % of the *Butyribacter* and/or the metabolites thereof, based on the total weight of the composition.

In another preferred embodiment, the composition is in a unit dosage form (one tablet, one capsule or one vial) and the weight of the composition in each unit dosage form is from 0.05 to 5 g, preferably from 0.1 to 1 g.

In another preferred embodiment, the composition further comprises other probiotics and/or prebiotics.

In another preferred embodiment, the probiotic is selected from the group consisting of lactic acid bacteria, bifidobacteria, *Lactobacillus acidophilus*, and a combination thereof.

In another preferred embodiment, the prebiotic is selected from the group consisting of fructooligosaccharide (FOS), galactooligosaccharide (GOS), xylooligosaccharide (XOS), lactosucrose (LACT), soybean oligosaccharides (SOS), Inulin, and a combination thereof.

The third aspect of the present invention is to provide a use of a *Butyribacter* according to the first aspect of the present invention or a composition according to the second aspect of the present invention for preparing medicament, the medicament is for one or more of the uses selected from the group consisting of: (a) prevention and/or treatment for obesity; (b) reduction of blood fat; (c) prevention or treatment for cardiovascular disease; and/or (d) prevention and/or treatment for diabetes.

The fourth aspect of the present invention is to provide a use of the *Butyribacter* according to the first aspect of the present invention or the composition according to the second aspect of the present invention for preparing a medicament or a preparation, the medicament or the preparation is used for (i) reducing the level of monocyte chemotactic protein (MCP-1) in mammals; and/or (ii) improving leptin resistance, increasing sensitivity to leptin in vivo.

In another preferred embodiment, the medicament or the preparation is also independently or additionally, for one or more of the uses selected from the group consisting of:
(iii) inhibition of weight gain in mammals;
(iv) reduction of body fat percentage (a ratio of fat weight to body weight) in mammals;
(v) reduction of blood lipids level in mammals;
(vi) increase of high density lipoprotein (HDLC) level in mammals;
(vii) reduction of low density lipoprotein (LDLC) level in mammals.

In another preferred embodiment, the mammal comprises human, or a rodent (such as a rat, or a mouse).

In another preferred embodiment, the reduction of blood lipids level in mammals comprises the reduction of total cholesterol (TC) level and/or triglyceride level.

The fifth aspect of the present invention is to provide a method for preparing the composition according to the second aspect of the present invention, comprising a step of:
mixing the *Butyribacter* and/or the metabolites thereof according to the first aspect of the present invention with a food acceptable carrier or a pharmaceutically acceptable carrier to form a composition according to the second aspect of the present invention.

In another preferred embodiment, the composition is an oral preparation.

The sixth aspect of the present invention is to provide a production method comprising the following steps:
(a) cultivating the *Butyribacter* according to the first aspect of the present invention under a condition suitable for culturing, thereby obtaining a culture product;
(b) optionally, isolating *Butyribacter* bacteria cells and/or metabolites thereof from the culture product; and
(c) optionally, mixing the obtained *Butyribacter* bacteria cells and/or the metabolites isolated from the previous step with a food acceptable carrier or pharmaceutically acceptable carrier, thereby obtaining a composition.

The seventh aspect of the present invention is to provide a method for reducing weight and/or blood lipid, comprising administering the *Butyribacter* according to the first aspect of the present invention or the composition according to the second aspect of the present invention to a subject in need.

In another preferred embodiment, the administration comprises oral administration.

In another preferred embodiment, dosage for administering is 0.01-5 g/50 kg body weight/day, preferably is 0.1-2 g/50 kg body weight/day.

In another preferred embodiment, the subject comprises a mammal, such as a human.

It should be understood that, within the scope of the present invention, each technical feature of the present invention described above and in the following (as examples) may be combined with each other to form a new or preferred technical solution, which is not listed here due to space limitations.

DETAILED DESCRIPTION

Figure 1:
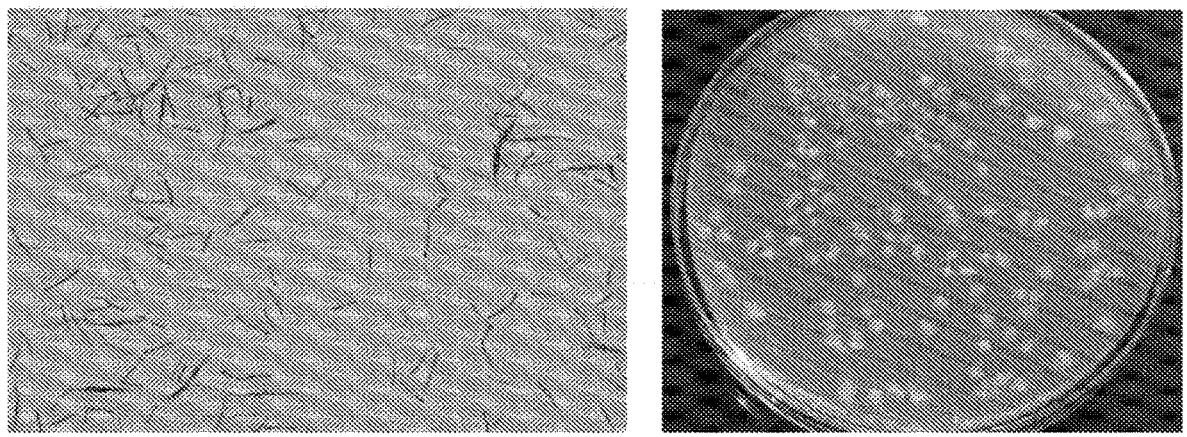
FIG. 1 shows the image of the colonies and the microscopic image (1000 fold) after gram staining of *Butyribacter* (*Butyribacter intestini* TF01-11) of the present invention.

Upon extensive and intensive studies and experiments, the inventors have unexpectedly found that *Butyribacter* (*Butyribacter intestini*) has the effect of preventing and treating obesity and obesity-associated diseases, such as cardiovascular diseases. After being fed to the experimental subjects, the active composition containing *Butyribacter* is found to possess the ability to inhibit weight gain, increase body-fat ratio, lower blood lipid, and effectively alleviate cardiovascular disorder, obesity and other diseases. On this basis, the inventors completed the present invention.

As used herein, the term "comprising" means that various ingredients may be together employed in a mixture or composition of the present invention. Thus, the term "consisting essentially of" and "consisting of" are encompassed in the term "comprising".

As used herein, the term "body-fat ratio" refers to the ratio of fat weight to body weight.

*Butyribacter* and Use Thereof

As used herein, the terms "*Butyribacter*" and "*Butyribacter intestini*" can be used interchangeably. In a preferred embodiment, the strain is *Butyribacter intestini* TF01-11 with a deposit number of CGMCC 10984, isolated from human faeces. Physiological characteristics of *Butyribacter* are shown as follows: *Butyribacter* is cultured on PYG plate under anaerobic conditions for 48 h at 37° C. and then the colonies present an off-white, opaque, smooth outlook with a pseudo-root like irregular edge, and the diameter of the colony is about 2 mm. After the Gram staining, the microscopic observation shows that TF01-11 is a non-sporle, Gram-positive bacteria with long rod-shape. It has flagella and can move. The diameter of the bacteria is about 0.5-1.0 mm, and the length of which is about 2.0-8.0 mm. Besides, the *Butyribacter* of the present invention is a catalase-negative bacterium. The temperature for growth ranges from 30° C. to 42° C., and the optimum growth temperature is 37° C. The pH tolerance range is 6.0-8.5, and it can tolerate 2% of NaCl. Several carbohydrates, including xylose, galactose, raffinose, glucose, maltose, cellobiose, sucrose, starch or glycogen, can be used for fermentation, and the acetic acid and butyric acid are the main products.

A use of *Butyribacter* in the treatment and prevention of obesity and obesity-associated diseases, such as cardiovascular diseases is provided by the present invention. High-fat food is taken by the subjects, and the strains of *Butyribacter intestini* TF01-11 have the ability of (i) suppressing the weight gain of the subject; (ii) reducing the blood lipid; and (iii) increasing the body-fat ratio. According to a preferred embodiment of the present invention, compared with the untreated control group, the weight gain of the male C57BL/6J mice fed with high-fat food which may lead to obesity and then treated with the strains of *Butyribacter intestini* TF01-11 increased slower than those without treatment and the blood lipid decreased. Various indicators associated with obesity or cardiovascular disease, such as leptin (LEP) and monocyte chemoattractant protein (MCP-1), also dropped. Therefore, the strain can be used to prevent and treat obesity and the diseases caused by obesity, such as cardiovascular diseases and the like.

Composition and the Use Thereof

A composition, preferably a pharmaceutical composition, is provided by the present invention. The composition comprises an effective amount of *Butyribacter*. In a preferred embodiment, the composition further comprises the probiotics selected from the group consisting of lactic acid bacteria, bifidobacteria, *Lactobacillus acidophilus*, and the combination thereof; and/or prebiotics selected from the group consisting of fructooligosaccharide (FOS), galactooligosaccharide (GOS), xylooligosaccharide (XOS), lactosucrose (LACT), soybean oligosaccharides (SOS), Inulin, and combination thereof.

In a preferred embodiment, the composition is a liquid preparation, a solid preparation, or a semi-solid preparation.

In a preferred embodiment, the liquid preparation is selected from the group consisting of a solution product or a suspension product.

In a preferred embodiment, the dosage form of the composition is selected from the group consisting of a powder, pulvis, tablet, sugar coating agent, capsule, granule, suspension, solution, syrup, drop, and sublingual tablet.

The pharmaceutical composition of the present invention may be administered in any form selected from the group consisting of a pharmaceutical tablet, injection and capsule. The pharmaceutical composition comprises an excipient, and a pharmaceutically acceptable vehicle or a carrier, and these substances may be selected according to the administration route. The pharmaceutical preparations in the present invention may further contain auxiliary active ingredients.

Lactose, glucose, sucrose, sorbitol, mannose, starch, acacia, calcium phosphate, alginate, gelatin, calcium silicate, fine crystalline cellulose, polyvinylpyrrolidone (PVP), cellulose, water, syrup, methyl cellulose, methyl hydroxybenzoate, propyl 4-hydroxybenzoate, talc, magnesium stearate, or mineral oil and the like can all be used as a carrier, excipient or diluent and the like in the pharmaceutical composition of the present invention.

In addition, the pharmaceutical composition of the present invention may further include a lubricant, wetting agent, emulsifying agent, suspension stabilizer, preservative, sweetener and fragrance and the like. The pharmaceutical composition of the present invention can be produced as enteric-coated preparations by various well-known methods so that the active ingredient of the pharmaceutical composition, that is, the microorganisms, can successfully pass through the stomach without being destroyed by gastric acid.

In addition, the microorganism of the present invention can be used in the form of a capsule prepared by a conventional method. For example, a standard excipient is mixed with the freezing-dried microorganisms of the present invention, thereby forming a pellet pill, and then the pill is filled into a gelatin capsule. Further, the micro-organisms of the present invention can be mixed with a pharmaceutically acceptable excipient, such as a liquid gum, cellulose, silicate or mineral oil and the like to prepare a suspension or a dispersion liquid, which can be filled into a soft gelatin capsules.

The pharmaceutical composition of the present invention can be made into enteric-coated tablets for oral use. The term "enteric coating" in the present application includes all the conventional and pharmaceutically acceptable coatings. These coatings cannot be degraded by gastric acid but can be sufficiently decomposed in the small intestine and rapidly release the microorganisms of the present invention. The enteric coating of the present invention can be maintained in a synthetic gastric acid, such HCl solution (pH=1), for more than 2 hours at 36-38° C. and preferably can decompose within 1.0 hour in a synthetic intestinal fluid, such as buffer with a pH of 7.0.

The enteric coating of the present invention is coated at about 16-30 mg per tablet, preferably 16-25 mg, more preferably 16-20 mg. The thickness of the enteric coating in the present invention is 5-100 um, and the ideal thickness is 20-80 um. The ingredient of the enteric coating is selected from conventional polymers that are well known to the public.

The preferred enteric coating of the present invention can be prepared from a copolymer of a cellulose acetate phthalate polymer or a trimellitate polymer and a methacrylic acid (for example, a methacrylic acid copolymer containing 40% or more of methacrylic acid and methylcellulose hydroxypropyl phthalate or the ester derivatives thereof).

The cellulose acetate phthalate used in the enteric coating of the present invention has a viscosity of about 45-90 cp. The content of the acetyl is 17-26%, and the content of orthophthalic acid is 30-40%. The cellulose acetate diphenyl ester used in the enteric coating has a viscosity of about 5-21 cs. The content of acetaphthalein is 17-26%. The cellulose acetate trimellitate manufactured by Eastman Keda Company can be used for the enteric coating materials in the present invention.

The hydroxypropylmethylcellulose phthalate used in the enteric coating of the present invention typically has a molecular weight of 20,000-130,000 Daltons, and the ideal molecular weight is 80,000-100,000 Daltons. The content of the hydroxypropyl is 5-10%, the methoxy content is 18-24% and the phthaloyl content is 21-35%.

The hydroxypropylmethylcellulose phthalate used in the enteric coating of the present invention is HP50, produced by Shin-Etsu Chemical Co., Ltd., Japan. HP50 contains 6-10% of hydroxypropyl, 20-24% of methoxy, 21-27% of propyl with a molecular weight of 84,000 Daltons. Another enteric coating material is HP55, and HP55 contains 5-9% of hydroxypropyl methylcellulose phthalate, 18-22% of methoxy, 27-35% of phthalic acid with a molecular weight of 78,000 Daltons.

The enteric coating of the invention is prepared by spraying the enteric coating solution onto the core using conventional methods. All of the solvents in the enteric coating process are selected from alcohols (such as, ethanol), ketones (such as, acetone), halogenated hydrocarbon compounds (such as, methylene chloride), and the combinations thereof. The softener, such as di-n-butyl phthalate or triacetin, is added into the enteric-coated solution at a ratio of about 1 part of the coating to about 0.05 parts or about 0.3 parts of a softener. The spraying method is preferably continuously carried out and the amounts of spraying materials can be controlled according to the conditions used for the coating. Spraying pressure can be adjusted randomly. In general, the desired results can be obtained at an average pressure of 1-1.5 bar.

The term "pharmaceutically effective amount" in the specification refers to an amount that is functional and active to humans and/or animals and acceptable to humans and/or animals. For example, in the present invention, a preparation contains $1\times10$-$1\times10^{20}$ cfu/ml or cfu/g (particularly, $1\times10^{4}$-$1\times10^{15}$ cfu/ml or cfu/g; more particularly, $1\times10^{6}$-$1\times10^{11}$ cfu/ml or cfu/g) of *Butyribacter* and/or a metabolite thereof.

When used for the preparation of pharmaceutical compositions, the effective dosage of *Butyribacter* or the metabolites thereof may vary depending on the mode of administration and the severity of the disease to be treated. Dosage forms suitable for oral administration include about $1\times10$-$1\times10^{20}$ cfu/ml or cfu/g (particularly, $1\times10^{4}$ to $1\times10^{15}$ cfu/ml or cfu/g; more particularly $1\times10^{6}$ to $1\times10^{11}$ cfu/ml or cfu/g) of the active *Butyribacter* or fermentation-produced active ingredients, in a close mixture with a solid or a liquid pharmaceutically acceptable carrier. This dosing regimen can be adjusted to provide the best therapeutic response. For example, depending on the urgency of the treatment condition, several divided doses may be administered daily, or the dose may be proportionally reduced.

The *Butyribacter* or the metabolites thereof can be administered by oral administration and the like. Solid carriers include starch, lactose, dicalcium phosphate, microcrystalline cellulose, sucrose and kaolin, while liquid carriers include: medium, polyethylene glycol, nonionic surfactants and edible oils (such as corn oil, peanut oil, and sesame oil), as long as it is suitable for the properties of the *Butyribacter* or the metabolites thereof and the desired particular mode of administration. Adjuvant commonly used in the preparation of pharmaceutical compositions may also be advantageously included, for example, flavors, coloring agents, preservatives and antioxidants such as vitamin E, vitamin C, BHT and BHA.

In order to facilitate preparation and administration, the preferable pharmaceutical compositions are solid compositions, especially tablets and solid-filled or liquid-filled capsules. Oral administration is preferred.

The composition of the invention is administered to the individual one or more times per day. The dosage unit means that the dose is formally separable and suitable for human or other mammalian individual. Each unit contains a pharmaceutical-acceptable carrier and a therapeutically effective amount of the microorganism of the present invention. The amount to be administered varies with the weight of the patient, the severity of the obesity, the included supplementary active components and the employed microorganisms. In addition, if possible, they can be administered separately and, if necessary, they can be administered continuously. Thus, the amounts for administration will not limit the invention. In addition, the "composition" in the present invention not only means medicines but also functional food and health supplements. In a preferred embodiment, the composition comprises: beverages, foods, medicines, animal feeds and the like.

In a preferred embodiment of the present invention, a food composition is further provided, comprising an effective amount of *Butyribacter* and/or a metabolite thereof, and the rest food acceptable carrier, the dosage form of the food composition is selected from the group consisting of a solid, dairy product, solution product, powder product, and suspension product.

In a preferred embodiment, the formulation of the composition is shown as follows:

$1\times10$-$1\times10^{20}$ cfu/mL of *Butyribacter* and/or the metabolites thereof; and a food or pharmaceutically acceptable carrier, and/or an excipient.

In another preferred embodiment, the formulation of the composition is shown as follows:

$1\times10^{6}$-$1\times10^{11}$ cfu/mL of *Butyribacter* and/or the metabolites thereof; and a food or pharmaceutically acceptable carrier, and/or an excipient.

Production Method for *Butyribacter*

Generally, *Butyribacter* can be prepared by conventional methods.

In the present invention, a method capable of producing *Butyribacter* on a large scale is provided. In particular, the following steps are included:

(a) under conditions suitable for culturing, cultivating the *Butyribacter*, thereby obtaining a culture product;

(b) optionally, isolating the *Butyribacter* bacteria cells and/or metabolites thereof from the culture product; and (c) optionally, mixing the isolated *Butyribacter* bacteria cells and/or their metabolites obtained in the previous step with a food acceptable carrier or pharmaceutically acceptable carrier, thereby preparing a composition.

Method for Reducing the Weight and/or Blood Lipid

In another preferred embodiment, the method comprises: ingesting a pharmaceutical composition, a food composition, a beverage composition, or the combination thereof of the present invention. The subject is human.

In another preferred embodiment, the method comprises: ingesting a pharmaceutical composition, a food composition, or an animal feed of the invention, or a combination thereof. The subjects are animals, preferably mice and rabbits.

The main advantages of the present invention include:
(a) The *Butyribacter* of the present invention can significantly lower body weight, blood lipid and body-fat ratio.
(b) The *Butyribacter* of the present invention can significantly reduce the indicators (such as cholesterol and triglyceride) associated with obesity and the obesity-associated diseases such as cardiovascular diseases.
(c) The *Butyribacter* of the present invention can significantly reduce the level of total cholesterol, triglyceride, and low-density lipoprotein.
(d) The *Butyribacter* of the present invention can significantly increase the level of high-density lipoprotein.
(e) The *Butyribacter* of the present invention can improve insulin resistance and also can reduce the risk of atherosclerosis and cardiovascular disease.
(f) The *Butyribacter* of the present invention can significantly reduce the level of monocyte chemotactic protein-1 (MCP-1).
(g) The *Butyribacter* of the present invention can effectively improve the leptin resistance accompanied with obesity and increase the sensitivity to Leptin in vivo.

The present invention is further described below with reference to specific embodiments. It should be understood that these examples are only for illustrating the present invention and not intended to limit the scope of the present invention. The conditions of the experimental methods not specifically indicated in the following examples are usually in accordance with conventional conditions as described in Sambrook et al., Molecular Cloning: A Laboratory Manual (New York: Cold Spring Harbor Laboratory Press, 1989), or according to the conditions described in the Journal of Microbiology: An Experimental Handbook (edited by James Cappuccino and Natalie Sherman, Pearson Education Press) or the manufacturer's proposed conditions.

Example 1: Screening and Identification of *Butyribacter* (*Butyribacter intestini* TF01-11)

1.1 Isolation of *Butyribacter intestini* TF01-11

*Butyribacter intestini* TF01-11 of the present invention was isolated from a faeces sample of a 17-year-old man in Yantian District of Shenzhen City. About 0.2 g of faeces sample was taken under anaerobic conditions, added into a sterile Phosphate Buffered Saline (PBS), and then subjected to gradient dilution coating. A Peptone Yeast Glucose Broth (PYG medium was used, the main components of which were 5 g of peptone, 5 g of trypticase peptone, 10 g of yeast powder, 5 g of beef extract, 5 g of glucose, 2 g of $K_2HPO_4$, 1 ml of TWEEN 80 (Polysorbate 80 or Polyoxyethylene sorbitan monooleate), 0.5 g of Cysteine-HCl.$H_2O$, 5 mg of heme, 1 ul of vitamin $K_1$, 40 ml of inorganic salt solution (each liter of inorganic salt solution containing 0.25 g of $CaCl_2.2\ H_2O$, 0.5 g of $MgSO_4.7\ H_2O$, 1 g of $K_2HPO_4$, 1 g of $KH_2PO_4$, 10 g of $NaHCO_3$, 2 g of NaCl), 1 mg of resazurin, 950 ml of distilled water, pH6.8-7.0, sterilized at 115° C. for 25 min. After 48 hours of plate culture, single colony was picked for the coating and separation.

1.2 Identification for 16S rDNA 1 ml of cultured bacteria cells of TF01-11 was taken, the genomic DNA was extracted, and the 16S rDNA was amplified with a primer pair of 8f/1492r by PCR.

The resulting amplification product was purified and sequenced to obtain a 1400 bp of 16S rDNA sequence (as shown in SEQ ID NO.: 1). The sequence was compared with the database to obtain *Roseburia intestinalis*, which had the highest identity with the 16S rDNA of TF01-11 as 92.18%.

SEQ ID No.: 1

```
tgcagtcgaa cgaagctcct gcgacagatt ccttcgggat gaagatgctt gagacttagt   60
ggcggacggg tgagtaacgc gtgggtaacc tgccctgtac tgggggacaa cagttagaaa  120
tgactgctaa taccgcataa gcctacggag tcgcatgact cagcaggaaa aattccggtg  180
gtacaggatg ggcccgcgtc tgattagcta gttggtgagg taatggctca ccaaggcgac  240
gatcagtagc cggcttgaga gagtgaacgg ccacattggg actgagacac ggcccaaact  300
cctacgggag gcagcagtgg ggaatattgc acaatggggg aaaccctgat gcagcaacgc  360
cgcgtgagtg aagaagtatt tcggtatgta aagctctatc agcagggaag aaaatgacgg  420
tacctgacta agaagcaccg gctaaatacg tgccagcagc cgcggtaata cgtatggtgc  480
aagcgttatc cggatttact gggtgtaaag ggagcgcagg cggtctggca agtctgatgt  540
gaaaatccgg ggctcaactc cggaactgca ttggaaactg tcagactaga gtgtcggaga  600
ggtaagtgga attcctagtg tagcggtgaa atgcgtagat attaggagga acaccagtgg  660
cgaagggcgg cttactggac gataactgac gctgaggctc gaaagcgtgg ggagcaaaca  720
ggattagata ccctggtagt ccacgccgta aacgatgaat actaggtgtc ggggcacaaa  780
agtgcttcgg tgccgcagca aacgcattaa gtattccacc tggggagtac gttcgcaaga  840
atgaaactca aaggaattga cggggacccg cacaagcggt ggagcatgtg gtttaattcg  900
aagcaacgcg aagaaccttta ccagtccttg acatcccgat gaccgacctg taacgaggtc  960
ttctcttcgg agcatcggag acaggtggtg catggttgtc gtcagctcgt gtcgtgagat 1020
```

```
gttgggttaa gtcccgcaac gagcgcaacc cctgtcctta gtagccagca gttcggctgg 1080
gcactctagg gagactgccg gggataaccc ggaggaaggt ggggacgacg tcaaatcatc 1140
atgcccctta tgggctgggc tacacacgtg ctacaatggt gctaacaaag tgaagcaagc 1200
tggtgacagt aagcaaatca caaaaatggc atctcagttc ggattgtagt ctgcaactcg 1260
actacatgaa gctggaatcg ctagtaatcg cagatcagaa tgctgcggtg aatacgttcc 1320
cgggtcttgt acacaccgcc cgtcacacca tgggagttgg aaatgcccga agtcagtgac 1380
ccaaccgcaa ggagggagca                                              1400
```

1.3 Evolution Analysis of *Butyribacter intestini* TF01-11

Multiple sequence alignment of the 16S rDNA sequences of TF01-11 and model Species of the Lachnospiraceae was carried out, then evolutionary tree was constructed by MEGA 5 and phylogenetic tree was constructed by using Neighbor-joining method.

1.4 Microbiological Characteristics of *Butyribacter intestini* TF01-11

(1) Morphological Characteristics

*Butyribacter* (*Butyribacter intestini* TF01-11) exhibited an off-white, opaque, smooth outlook with pseudo-root like irregular edge and a colony diameter of about 2 mm (FIG. 1) after cultured on plate containing PYG medium (PYG plate) under anaerobic conditions for 48 h at 37° C.

(2) Microscopic Features

Through gram staining, microscopic observation showed that TF01-11 was non-spore Gram-positive bacteria with long rod-shape. It had flagella possessed moving ability. The diameter of the bacteria cells was about 0.5-1.0 mm, and the length was about 2.0-8.0 mm (FIG. 1).

(3) Physiological and Biochemical Characteristics

TF01-11 was negative to catalase. The temperature for growth ranged from 30° C. to 42° C., and the optimum growth temperature was 37° C. The pH tolerance range is 6.0-8.5, and it can tolerate 2% of NaCl. After comparing the enzyme reaction (API ZYM) and the substrate utilization (API 20A, API 50CH) of TF01-11 with three *affinis* model strains (*Roseburia intestinalis* DSM 14610$^T$; *Acetobrio ethanolgignens* ATCC 33324$^T$; *Lachnospira multipara* DSM 3073$^T$), Table 1 showed that there was a large difference in the API response with those three *affinis* model strains and TF01-11.

TABLE 1

| substrate | TF01-11 | *R. intestinalis* DSM 14610 | *A. ethanolgignens* ATCC 33324 | *L. multipara* DSM 3073 |
|---|---|---|---|---|
| tryptophan (indole generation) | − | − | − | − |
| urea (urease) | − | − | − | − |
| glucose | + | + | + | + |
| mannitol | − | − | + | − |
| lactose | − | − | + | − |
| sucrose | − | + | − | + |
| maltose | − | − | + | − |
| salicin | − | − | + | + |
| xylose | − | + | − | + |
| arabinose | − | + | − | − |
| gelatin hydrolysate | + | − | + | − |
| esculin/ferric citrate | − | + | − | + |
| glycerinum | − | − | − | − |
| cellose | − | − | +− | + |
| mannose | − | − | + | − |
| melezitose | − | − | − | − |
| raffinose | − | + | +− | − |
| sorbitol | − | − | − | − |
| rhamnose | − | − | − | − |
| trehalose | − | − | − | − |
| enzyme reaction (API ZYM) | | | | |
| control | − | − | − | − |
| alkaline phosphatase. | − | − | − | − |
| esterase (C4) | − | + | − | − |
| lipid esterase (C8) | − | +− | − | − |
| lipid enzyme (C14) | − | − | − | − |
| leucinearylamidase | − | − | + | +− |
| valinearylamidase | − | − | − | − |
| cystinearylamidase | − | − | − | − |
| trypsin | − | − | − | − |
| chymotrypsin | − | − | − | − |
| acid phosphatase ACP | +− | − | − | + |
| naphthol-AS-BI-phosphohydrolase | + | + | + | + |

TABLE 1-continued

| substrate | TF01-11 | R. intestinalis DSM 14610 | A. ethanolgignens ATCC 33324 | L. multipara DSM 3073 |
|---|---|---|---|---|
| α-galactosidase | − | + | − | − |
| β-galactosidase | − | + | − | − |
| β-glucuronidase | − | +− | − | − |
| α-gluconase | + | − | − | − |
| β-gluconase | − | +− | − | − |
| N-acetyl-glucosamine | − | − | − | − |
| α-mannosidase | − | − | − | − |
| β-AFU | − | − | − | − |

(4) The analysis on the cell fatty acid composition of TF01-11 and 3 affinis model strains were conducted and the results are shown as follows (strain: 1, TF01-11$^T$; 2, Roseburia intestinalis DSM 14610$^T$; 3, Acetivibrio ethanolgignens ATCC 33324$^T$; 4, Lachnospira multipara DSM 3073$^T$; -, not detected)

| fatty acid | chemical name of fatty acid | 1 | 2 | 3 | 4 |
|---|---|---|---|---|---|
| $C_{10:0}$ | saturated fatty acids with ten-carbon | — | — | 1.09 | — |
| $C_{12:0}$ | saturated fatty acids with twelve-carbon | — | 1.38 | 1.65 | — |
| $C_{13:1}$ | monounsaturated fatty acids with thirteen-carbon | 5.12 | — | 1.11 | 1.37 |
| $C_{14:0}$ | saturated fatty acids with fourteen-carbon | 16.35 | 9.20 | 13.30 | 8.00 |
| $C_{13:0}$ 3OH/iso-$C_{15:1}$ H | 3-hydroxytridecyl-saturated fatty acid /H-type heterogeneous fifteen-carbon monounsaturated fatty acids | 11.07 | — | 2.26 | 3.77 |
| $C_{16:1}$ ω9c | ω9c-C16 saturated fatty acid | — | — | 3.83 | — |
| $C_{16:1}$ ω7c/ $C_{16:1}$ ω6c | ω7c-C16 monounsaturated fatty acids /ω6c-C16 monounsaturated fatty acids | — | 6.14 | 4.98 | — |
| $C_{16:0}$ | C16 saturated fatty acids | 37.93 | 33.89 | 32.46 | 44.03 |
| $C_{17:1}$ ω8c | ω8c-seventeen-carbon monounsaturated fatty acids | 1.31 | — | — | — |
| Iso-$C_{17:1}$ I/anteiso B | I-type / B-type trans-17-C monounsaturated fatty acids | — | 1.20 | 3.89 | 7.90 |
| $C_{18:1}$ ω9c | ω9c-18-carbon monounsaturated fatty acids | 10.57 | 19.93 | 18.20 | 16.01 |
| $C_{18:1}$ ω7c | ω7c-18-carbon monounsaturated fat | 1.88 | 8.19 | 5.58 | 3.27 |
| $C_{18:1}$ ω6c | ω6c-18-carbon monounsaturated fat | — | 13.79 | 2.79 | — |
| $C_{18:0}$ | 18-carbon saturated fat | 2.42 | 4.79 | 5.15 | 5.18 |
| $C_{18:0}$ 2OH | 2-hydroxy octadecyl saturated fatty acid | — | — | — | 2.33 |
| Iso-$C_{19:0}$ | Hetero-nineteen-carbon saturated fatty acids | 4.32 | — | — | — |
| Iso-$C_{19:1}$ I | I-type isoproterenol monounsaturated fatty acids | — | — | — | 1.76 |
| $C_{19:1}$ ω9c/$C_{19:1}$ω11c | ω9c-nineteen-carbon monounsaturated fatty acids /ω11c-nineteen-carbon monounsaturated fatty acids | 3.43 | — | — | — |
| Anteiso-$C_{19:0}$ | anti-isotype-nineteen-carbon saturated fatty acids | — | — | — | 2.03 |

The results show that this strain is a new strain and it is further named as *Butyribacter intestini* TF01-11.

Example 2 Determination of the Biological Activity of *Butyribacter* (*Butyribacter intestini*) TF01-11)

1 ml of fermentation broth of TF01-11 cultured for 48 h was taken to centrifugation at 12000r/min for 5 min, and the supernatant was removed and diluted for 10 times with a certain concentration of formic acid aqueous solution (the final concentration of formic acid was 9%), ready for use. Measurement was carried out using external standard method, acetic acid, propionic acid, butyric acid, and pinalic acid were chosen for preparing the standard curve, wherein the concentration of acetic acid, butyric acid and pinalic acid was 517 μL/L, 497 μL/L, 401 μL/L, and 467 μL/L, respectively. The analysis was performed on a capillary column (30 m×0.25 mm×0.25 um) using a Shimadzu GC-2014C Gas Chromatography, HP-INNOWax (Cross-Linked PEG). The detector was a hydrogen flame ionization detector. The GC parameter was set as the column temperature: 180-200°

C.; Gasification chamber temperature: 240° C.; Detection temperature: 210° C.; Injection volume: 2 μL; Carrier gas flow rate: $N_2$, 50 mL/min; Hydrogen flow rate: 50 mL/min; air mass flow: 600-700 mL/min.

The results showed that the yield of short-chain fatty acid (SCFA) of TF01-11 determined by the above method is 2.79 mmol/L for acetic acid and 15.09 mmol/L for butyric acid.

Example 3 Therapeutic Effect of *Butyribacter* (*Butyribacter intestini* TF01-11) on Obesity Model Mice Experimental Materials:

Mice: Totally 30 of 6-week- old male C57BL/6J mice with normal feeding (purchased from Guangdong Medical Experimental Animal Center) were purchased. Mice were grown in the same environment and fed the same food.

Strain: The isolated and obtained *Butyribacter intestini* TF01-11 strain as described in Example 1

High-fat feed (HF): containing 78.8% of basic feed, 1% of cholesterol, 10% of egg yolk powder, 10% of lard and 0.2% of bile salt, purchased from Nantong Telofi Feed Technology Co., LTD.

General maintenance feed: purchased from Guangdong Medical Experimental Animal Center.

Experimental Method:

Normal adult male C57BL/6J mice were randomly divided into three experimental groups (Control group, obesity model group and TF01 group, respectively), with 10 mice in each group. The mice were allowed to eat and drink freely under the SPF (Specific Pathogen Free) environment. Fat model group (Model) and TF01 group were fed with high-fat feed, while control group was fed with common maintenance feed. After fed for 4 weeks, the TF01 group was subjected to gavage with *Butyribacter* (*Butyribacter intestini* TF01-11) bacteria liquid and Fat model group and the Control group were subjected to gavage with equal volume of medium for 9 weeks.

The volume of the bacteria for gavage was 0.15 mL/10 g body weight, and the bacteria concentration was $1\times10^7$ cfu/mL with a condensed concentration of $1\times10^8$ cfu/mL. The frequency was once every two days. The bacterial liquid should be cultured in advance and weekly activated to keep fresh, and the concentration was measured respectively.

During the experimental period, mice were recorded weekly for body weight, status, food intake and other data. During the last week of the experiment, mice in each group were subjected to oral glucose tolerance test (OGTT). After the experiment, the mice were sacrificed, the weight of fat was recorded, and the serum was taken. The content of blood lipid and protein factors was detected by Elisa kit.

The Experimental Results:

(1) Influence of *Butyribacter* (*Butyribacter intestini* TF01-11) on mice weight gain.

TABLE 1-2

| Group | 9 weeks (g) | P value-Model Group | P value-Control group |
|---|---|---|---|
| TF01 group | 7.38 | 0.001* | 0.075 |
| Model group | 13.25 | 1.000 | 0.000* |
| Control group | 5.37 | 0.000* | 1.000 |

Figure 2:
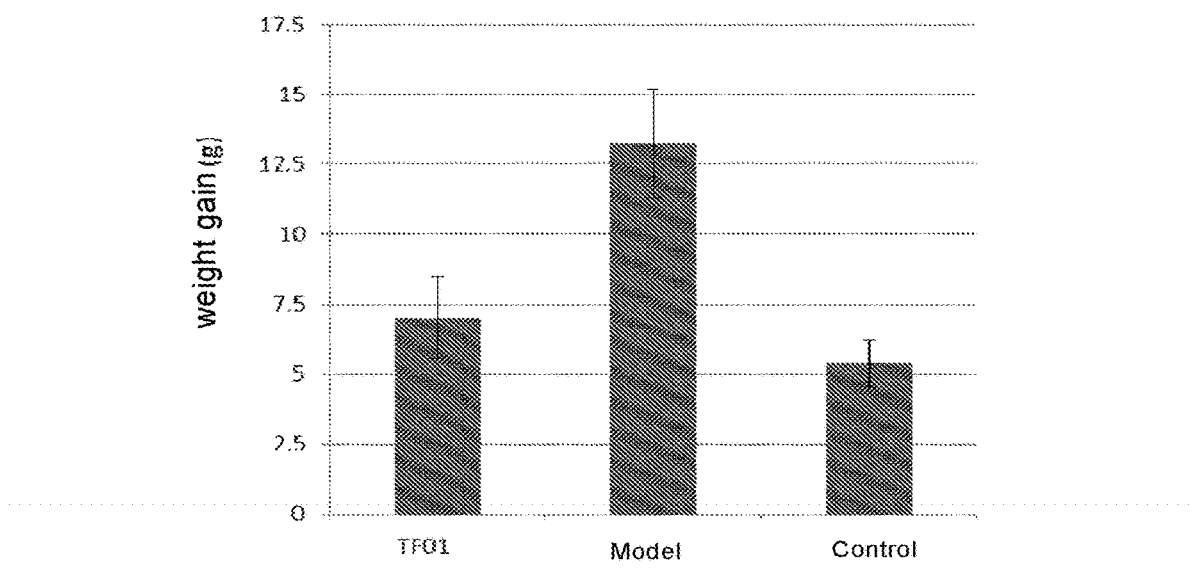
FIG. 2 shows compared to pre-gavage, the body weight gain of the mice in each group after a 9-week gavage of *B. intestini* TF01-11 (*Butyribacter*) bacterium solution.

The results are shown in Table 1-1, Table 1-2 and FIG. 2. The results show that *Butyribacter* (*Butyribacter intestini* TF01-11) can effectively reduce the increase in weight gain of obesity model mice (* P<0.05).

(2) Influence of *Butyribacter* (*Butyribacter intestini* TF01-11) on body-fat ratio.

TABLE 2 body-fat ratio in each group of mice

| Group | Fat weight/body weight × 100% | P value-Model group | P value-Control group |
|---|---|---|---|
| TF01 group | 3.931 | 0.000* | 0.056 |
| Model group | 7.366 | 1.000 | 0.000* |
| Control group | 2.822 | 0.000* | 1.000 |

Figure 3:
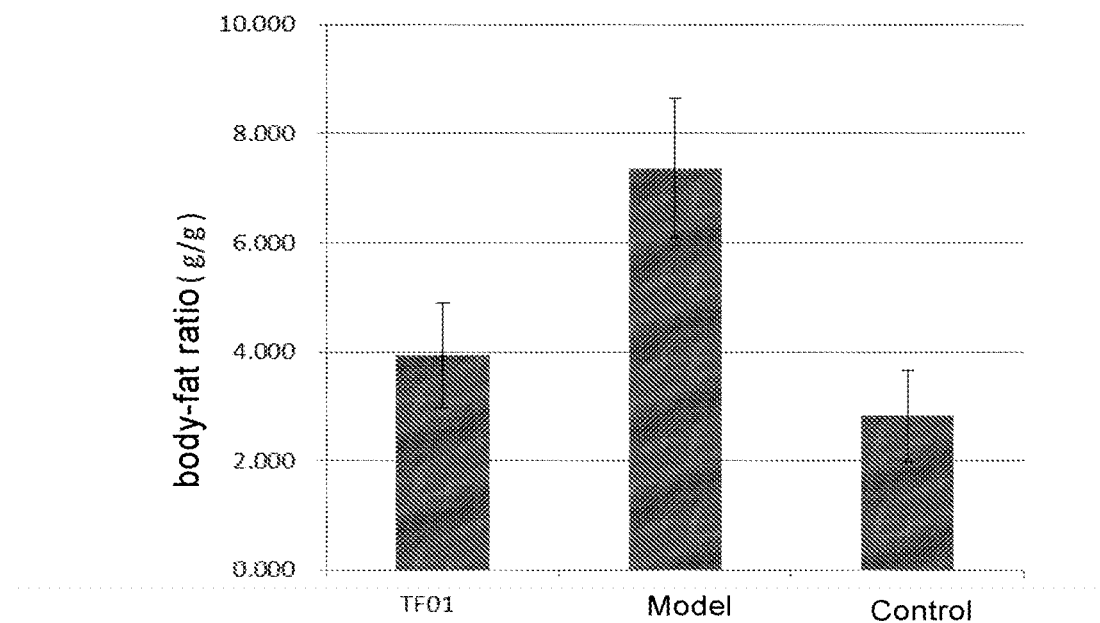
FIG. 3 shows the body-fat ratio of the mice in each group.

The results are shown in Table 2 and FIG. 3. The results show that *Butyribacter* (*Butyribacter intestini* TF01-11) can significantly reduce the body-fat ratio in obesity model mice (* P<0.05).

(3) Influence of *Butyribacter* (*Butyribacter intestini* TF01-11) on blood lipid.

TABLE 3

| Group | TC (total cholesterol) (mmol/L) | TG (triglyceride) (mmol/L) | LDLC (low density lipoprotein) (mmol/L) | HDLC (high-density lipoprotein) (mmol/L) |
|---|---|---|---|---|
| TF01 group | 4.866 | 1.023 | 1.400 | 3.486 |
| Model group | 6.308 | 1.281 | 2.372 | 2.148 |
| Control group | 3.815 | 0.938 | 1.247 | 3.300 |

TABLE 1-1

| group number | 1 week | 2 weeks | 3 weeks | 4 weeks | 5 weeks | 6 weeks | 7 weeks | 8 weeks | 9 weeks |
|---|---|---|---|---|---|---|---|---|---|
| TF01 group (g) | 1.87 | 2.83 | 3.38 | 4.50 | 5.13 | 5.37 | 6.50 | 7.02 | 7.38 |
| Model group(g) | 2.57 | 3.82 | 4.95 | 6.93 | 8.38 | 10.00 | 11.72 | 12.42 | 13.25 |
| Control group(g) | 1.43 | 2.13 | 2.57 | 3.35 | 4.55 | 4.48 | 5.32 | 5.22 | 5.37 |

TABLE 4

| P value | TC (total cholesterol) | TG (triglyceride) | LDLC (low density lipoprotein) | HDLC (high-density lipoprotein) |
| --- | --- | --- | --- | --- |
| TF01-Model | 0.006* | 0.034* | 0.018* | 0.046* |
| TF01-Control | 0.098 | 0.290 | 0.587 | 0.678 |
| Model-Control | 0.000* | 0.001* | 0.008* | 0.045* |

Figure 4:
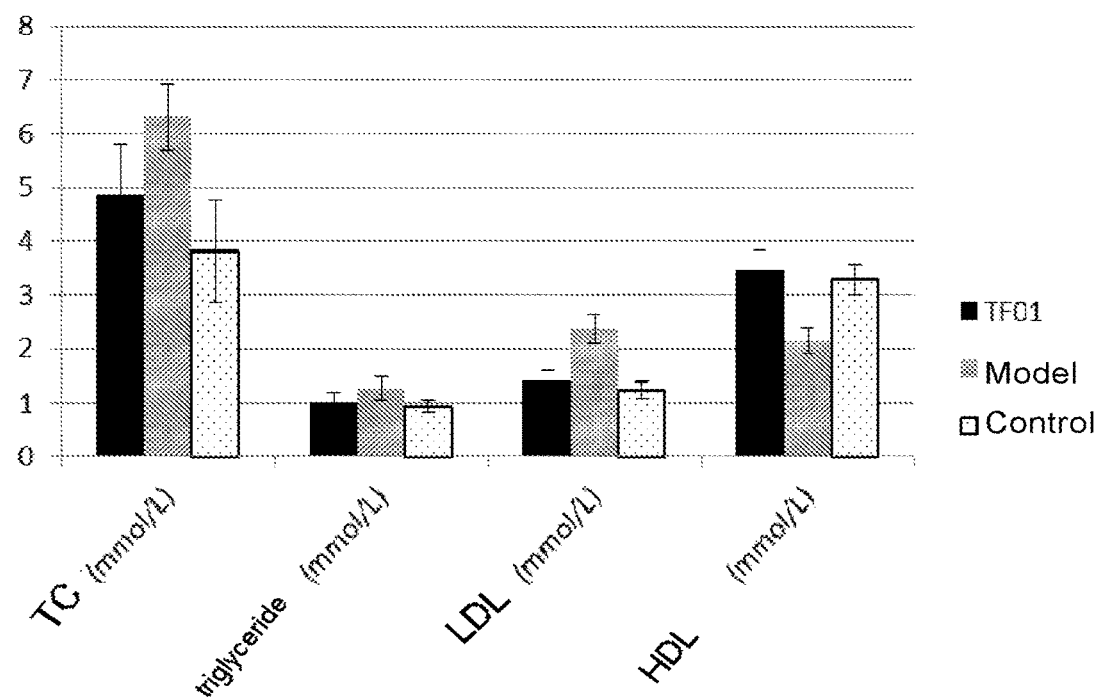
FIG. 4 shows the effect of *B. intestini* TF01-11 (*Butyribacter*) on blood lipid.

The results are shown in FIG. 4, Table 3 and Table 4. The main components of blood lipid are cholesterol and triglycerides. The increased levels of cholesterol and triglyceride in plasma are related to the development of atherosclerosis. The results show that Butyribacter (Butyribacter intestini TF01-11) can lower blood lipid and reduce the related indicators of atherosclerosis related diseases such as cardiovascular diseases. In addition, the effects of total cholesterol, triglyceride and low density lipoprotein (LDL) were significantly reduced, and the content of high density lipoprotein (HDL) was also significantly increased (* $P<0.05$).

(4) Influence of Butyribacter (Butyribacter intestini TF01-11) on Leptin (LEP), monocyte chemoattractant protein-1 (MCP-1).

TABLE 5

| Group | MCP-1 (pg/ml) | LEP (pg/ml) |
| --- | --- | --- |
| TF01 group | 337.6 | 1186.4 |
| Model group | 378.8 | 1398.8 |
| Control group | 340.4 | 1255.3 |

TABLE 6

| P value | MCP-1 | LEP |
| --- | --- | --- |
| TF01-Model | 0.014* | 0.014* |
| TF01-Control | 0.862 | 0.891 |
| Model-Control | 0.073 | 0.110 |

Figure 5:
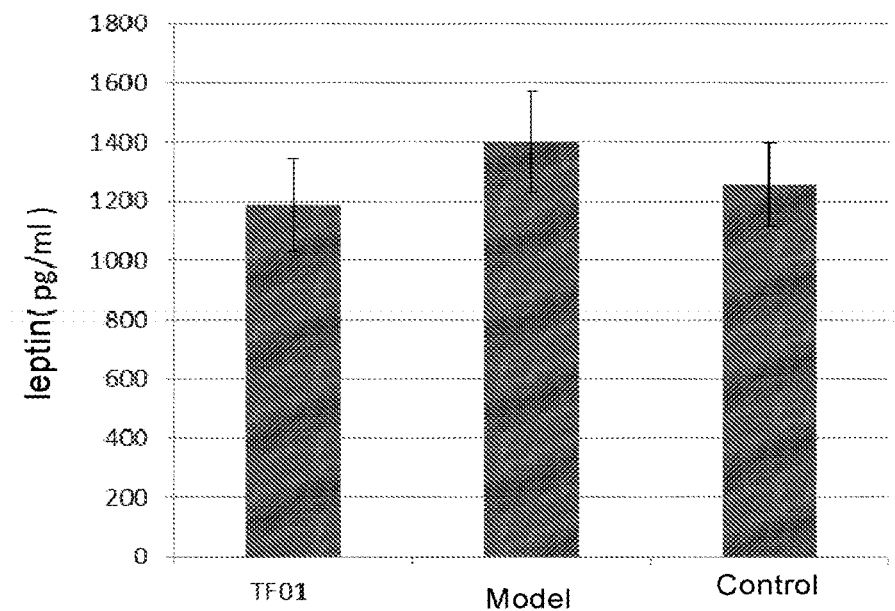
FIG. 5 shows the effect of *B. intestini* TF01-11 on Leptin (LEP).
Figure 6:
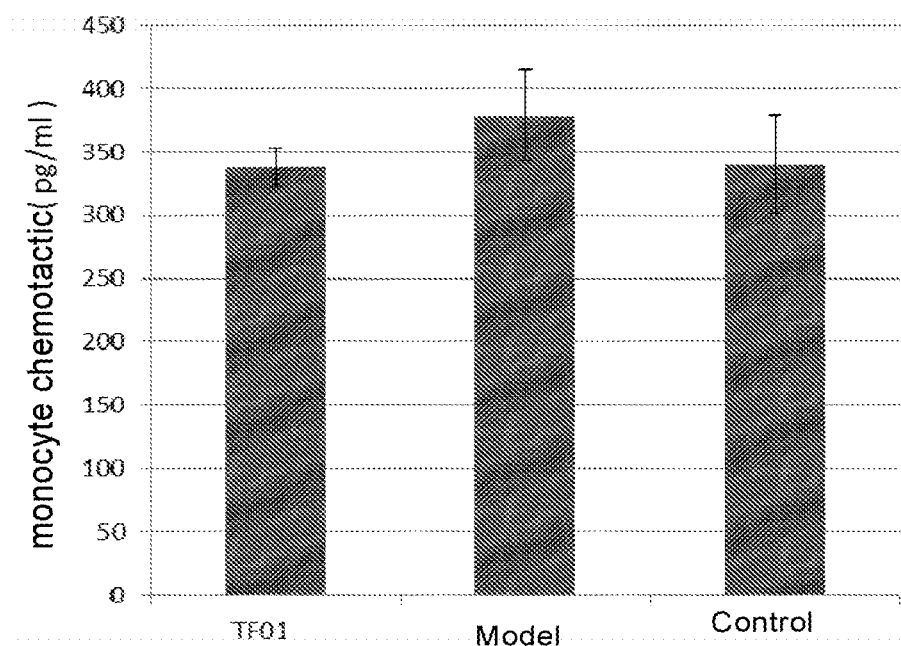
FIG. 6 shows the effect of *B. intestini* TF01-11 (*Butyribacter*) on monocyte chemotactic protein-1 (MCP-1).

The results are shown in FIG. 5, FIG. 6 and Table 5, and Table 6. The results show that Butyribacter (Butyribacter intestini TF01-11) can significantly reduce the levels of leptin (LEP) and MCP-1 in serum in obesity model mice (* $P<0.05$).

The results show that Butyribacter (Butyribacter intestini TF01-11) can improve the leptin resistance and increase the sensitivity to leptin (LEP) in vivo; and the level of serum MCP-1 was decreased after the treatment with Probiotics of Butyribacter intestini TF01-11, which is helpful to improve insulin resistance, and can reduce the risk of atherosclerosis and cardiovascular disease.

Example 4 Food Composition Containing Butyribacter Butyribacter Intestini TF01-11

Raw material ratio is as shown in Table 7.

TABLE 7

| Raw material | mass percent (%) |
| --- | --- |
| Butyribacter intestini TF01-11 | 0.5 |
| milk | 90.0 |
| sugar | 9.5 |

According to the proportion of the above formulation, milk and sugar were mixed and stirred until completely mixed, preheated and homogenized under 20 Mpa pressure, sterilized at 90° C. for 5-10 minutes, and cooled to 40-43° C. The product was inoculated with $1\text{-}100\times10^6$ cfu/g of Butyribacter intestini TF01-11 bacteria, thereby obtaining a food composition containing Butyribacter intestini TF01-11 bacteria.

Example 5 Pharmaceutical Composition Containing Butyribacter

Raw material ratio is as shown in Table 8.

TABLE 8

| Raw material | mass percent (%) |
| --- | --- |
| Butyribacter intestini TF01-11 | 1.0% |
| lactose | 2.0% |
| yeast powder | 2.0% |
| peptone | 1.0% |
| purified water | 94.0% |

According to the proportion, lactose, yeast powder, peptone and purified water were mixed evenly, preheated to 60-65° C., homogenized under 20 Mpa pressure, sterilized at about 90° C. for 20-30 minutes, and cooled to 36-38° C. The product was inoculated with $1\text{-}50\times10^6$ cfu/mL of Butyribacter intestini TF01-11 active bacteria, subjected to fermentation under 36-38° C. at a pH of 6.0, centrifuged, freezing-dried to a water content of less than 3%, thereby obtaining the freezing-dried Butyribacter intestini TF01-11. 0.5 g of freeze-dried Butyribacter intestini TF01-11 and maltodextrin with equivalent amount were mixed and filled into the capsule, thereby giving a pharmaceutical composition containing Butyribacter intestini TF01-11.

Deposit of Microorganisms

The strain of Butyribacter (Butyribacter intestini TF01-11) (with the same deposit name) of the present invention has been deposited at the China General Microbiological Culture Collection Center (CGMCC, address: No. 3, NO. 1 of West Beichen Road, Chaoyang District, Beijing, China) on Jun. 16, 2015, deposit number: CGMCC 10984.

All publications mentioned herein are incorporated by reference as if each individual document was cited as a reference, as in the present application. It should also be understood that, after reading the above teachings of the present invention, those skilled in the art can make various changes or modifications, equivalents of which falls in the scope of claims as defined in the appended claims.

The invention claimed is:

1. A method for treating obesity or obesity associated diseases in a subject, comprising administering a *Butyribacter intestini* having a sequence of 16s rDNA of SEQ ID NO: 1 or a composition comprising the *Butyribacter intestini* to the subject,
wherein the obesity associated diseases are atherosclerosis or cardiovascular disease.

2. The method according to claim 1, wherein the *Butyribacter intestini* is *Butyribacter intestini* TF01-11 deposited at the China General Microbiological Culture Collection Center with a deposit number of CGMCC 10984.

3. The method according to claim 1, wherein the composition further comprises a food acceptable or pharmaceutically acceptable carrier.

4. The method according to claim 3, wherein the food acceptable or pharmaceutically acceptable carrier is selected from excipient, lubricant, wetting agent, emulsifier, suspension stabilizer, preservative, sweetener or fragrance.

5. The method according to claim 1, wherein the composition further comprises one or both of probiotics and prebiotics.

6. The method according to claim 5, wherein the probiotics are Lactic acid bacteria, bifidobacteria, or a combination thereof.

7. The method according to claim 5, wherein the prebiotics are selected from the group consisting of fructooligosaccharide (FOS), galactooligosaccharide (GOS), xylooligosaccharide (XOS), lactosucrose (LACT), soybean oligosaccharides (SOS), Inulin or a combination thereof.

8. The method according to claim 1, wherein the composition comprises $10-1 \times 10^{20}$ cfu/mL or cfu/g of *Butyribacter intestini* TF01-11, based on total volume or total weight of the composition.

9. The method according to claim 1, wherein the composition comprises $1\times10^4$-$1\times10^{15}$ cfu/mL or cfu/g of *Butyribacter intestini* TF01-11, based on total volume or total weight of the composition.

10. The method according to claim 1, wherein the composition is of a dosage form selected from the group consisting of powder, pulvis, tablet, sugar coating agent, capsule, granule, suspension, solution, syrup, drop and sublingual tablet.

11. The method according to claim 1, wherein the composition is selected from the group consisting of: a food composition, a health care composition, a pharmaceutical composition, a beverage composition, a feed composition or a combination thereof.

12. The method according to claim 1, wherein the composition is in a unit dosage form of one tablet, one capsule or one vial, and the composition in each unit dosage form is of the weight from 0.05 to 5 g.

13. The method according to claim 1, wherein the *Butyribacter intestini* or the composition exhibits any activities from the group consisting of:
   (i) reducing monocyte chemotactic protein (MCP-1) level in a subject,
   (ii) improving leptin resistance and sensitivity to leptin in vivo,
   (iii) inhibiting weight gain in a subject,
   (iv) reducing body fat ratio in a subject,
   (v) reducing blood lipid level in a subject,
   (vi) increasing high-density lipoprotein (HDLC) level in a subject, and
   (vii) reducing low-density lipoprotein (LDLC) level in a subject.

14. The method according to claim 1, wherein the composition is administered orally.

15. The method according to claim 1, wherein the subject includes human or non-human mammal.

16. The method according to claim 1, wherein the administration dosage is 0.01-5 g/50 kg body weight/day.

17. A method capable of at least one of inhibiting weight gain, reducing body fat ratio or reducing blood lipid level in a subject having obesity, the method comprising administering a pharmaceutically effective amount of *Butyribacter intestini* having a sequence of 16s rDNA of SEQ ID NO: 1 or a composition comprising the *Butyribacter intestini* to the subject in need thereof.

* * * * *

SEQUENCE LISTING

<160> NUMBER OF SEQ ID NOS: 1

<210> SEQ ID NO 1
<211> LENGTH: 1400
<212> TYPE: DNA
<213> ORGANISM: Butyribacter intestini TF01-11

<400> SEQUENCE: 1

```
tgcagtcgaa cgaagctcct gcgacagatt ccttcgggat gaagatgctt gagacttagt      60
ggcggacggg tgagtaacgc gtgggtaacc tgccctgtac tggggacaa cagttagaaa      120 tgactgctaa taccgcataa gcctacggag tcgcatgact cagcaggaaa aattccggtg     180
gtacaggatg ggcccgcgtc tgattagcta gttggtgagg taatggctca ccaaggcgac      240
gatcagtagc cggcttgaga gagtgaacgg ccacattggg actgagacac ggcccaaact     300
cctacgggag gcagcagtgg ggaatattgc acaatggggg aaaccctgat gcagcaacgc     360
cgcgtgagtg aagaagtatt tcggtatgta aagctctatc agcagggaag aaaatgacgg     420
tacctgacta agaagcaccg gctaaatacg tgccagcagc cgcggtaata cgtatggtgc     480
aagcgttatc cggatttact gggtgtaaag ggagcgcagg cggtctggca agtctgatgt     540
gaaaatccgg ggctcaactc cggaactgca ttggaaactg tcagactaga gtgtcggaga     600
ggtaagtgga attcctagtg tagcggtgaa atgcgtagat attaggagga acaccagtgg     660
cgaagggcgg cttactggac gataactgac gctgaggctc gaaagcgtgg ggagcaaaca     720
ggattagata ccctggtagt ccacgccgta acgatgaat actaggtgtc ggggcacaaa     780
agtgcttcgg tgccgcagca aacgcattaa gtattccacc tggggagtac gttcgcaaga     840
atgaaactca aaggaattga cggggacccg cacaagcggt ggagcatgtg gtttaattcg     900
aagcaacgcg aagaacctta ccagtccttg acatcccgat gaccgacctg taacgaggtc     960
ttctcttcgg agcatcggag acaggtggtg catggttgtc gtcagctcgt gtcgtgagat    1020
gttgggttaa gtcccgcaac gagcgcaacc cctgtcctta gtagccagca gttcggctgg    1080
gcactctagg gagactgccg gggataaccc ggaggaaggt ggggacgacg tcaaatcatc    1140
atgcccctta tgggctgggc tacacacgtg ctacaatggt gctaacaaag tgaagcaagc    1200
tggtgacagt aagcaaatca caaaaatggc atctcagttc ggattgtagt ctgcaactcg    1260
actacatgaa gctggaatcg ctagtaatcg cagatcagaa tgctgcggtg aatacgttcc    1320
cgggtcttgt acacaccgcc cgtcacacca tgggagttgg aaatgcccga agtcagtgac    1380
ccaaccgcaa ggagggagca                                                1400
```